United States Patent [19]

Columbus

[11] 4,310,399

[45] Jan. 12, 1982

[54] LIQUID TRANSPORT DEVICE CONTAINING MEANS FOR DELAYING CAPILLARY FLOW

[75] Inventor: Richard L. Columbus, Rochester, N.Y.

[73] Assignee: Eastman Kodak Company, Rochester, N.Y.

[21] Appl. No.: 101,662

[22] Filed: Dec. 10, 1979

Related U.S. Application Data

[63] Continuation-in-part of Ser. No. 59,816, Jul. 23, 1979, abandoned.

[51] Int. Cl.³ .............................................. G01N 27/30
[52] U.S. Cl. .................................. 204/195 R; 422/58; 422/98
[58] Field of Search .......... 204/195 R, 195 F, 195 M; 23/230 R; 422/55–58, 98, 100

[56] References Cited

U.S. PATENT DOCUMENTS

| | | | |
|---|---|---|---|
| 3,055,759 | 9/1962 | Busby | 204/195 R |
| 3,151,052 | 9/1964 | Arthur et al. | 204/195 F |
| 3,498,289 | 3/1970 | Watanabe et al. | 204/195 F |
| 3,619,072 | 11/1971 | O'Hara et al. | 356/246 |
| 3,690,836 | 9/1972 | Buissiere et al. | 422/56 |
| 3,715,192 | 2/1973 | Wenz et al. | 422/56 |
| 3,853,732 | 12/1974 | Brand et al. | 204/195 F |
| 4,053,381 | 10/1977 | Hamblen et al. | 204/195 M |
| 4,184,936 | 1/1980 | Paul et al. | 204/195 M |

*Primary Examiner*—G. L. Kaplan
*Attorney, Agent, or Firm*—Dana M. Schmidt

[57] ABSTRACT

A liquid transport device is disclosed for providing capillary flow. The device features a capillary transport zone provided by two opposed surfaces and having at least two regions, and means extending between said regions for delaying flow of liquid therebetween.

19 Claims, 7 Drawing Figures

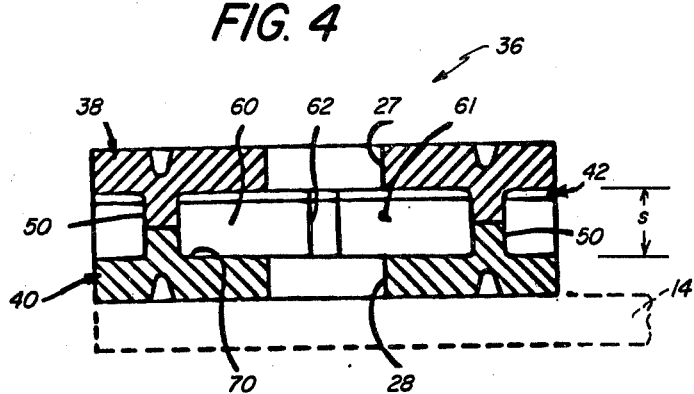
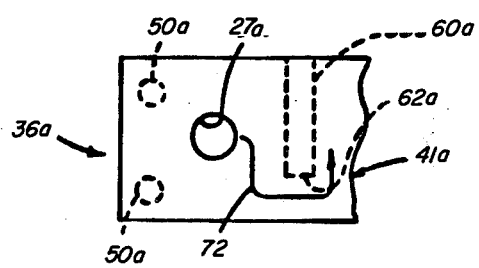
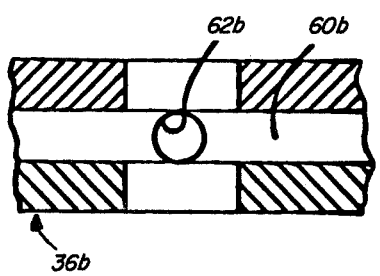
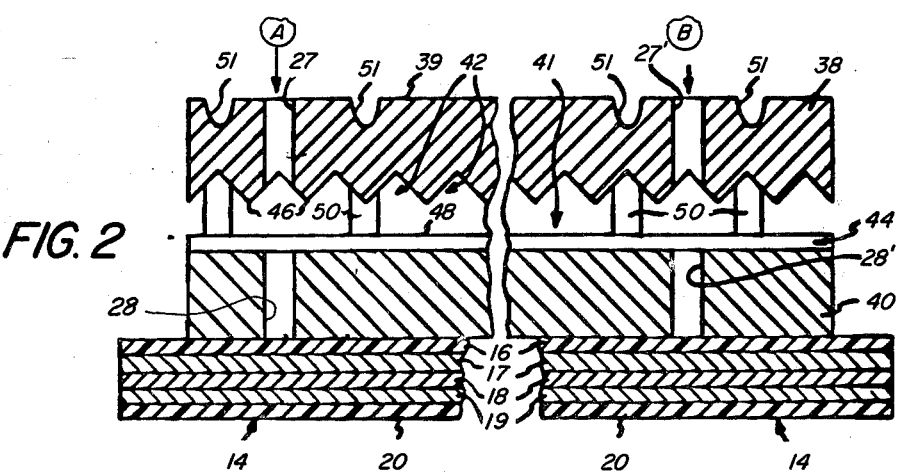

LIQUID TRANSPORT DEVICE CONTAINING MEANS FOR DELAYING CAPILLARY FLOW

RELATED APPLICATIONS

This application is a continuation-in-part application of U.S. Application Ser. No. 059,816, filed on July 23, 1979 and now abandoned.

FIELD OF THE INVENTION

This invention relates to a liquid transport device such as can be used for determining the activity and therefore the concentration of electrolytes in an aqueous solution. Such devices are valuable quantitative tools in the field of clinical chemistry to determine the existence and cause of certain body illnesses and abnormalities.

BACKGROUND OF THE INVENTION

My U.S. Application Ser. No. 954,689, now U.S. Pat. No. 4,233,029, entitled "Liquid Transport Device and Method", filed on Oct. 25, 1978, describes liquid transport members in which capillary attraction of the liquid between two opposed surfaces is used to distribute and transport the liquid. In that application, embodiments of such transport members are described for use with ion-selective electrodes (hereinafter ISE's). Such members have two opposed liquid transport surfaces spaced apart a distance effective to induce capillary flow of introduced liquid between the surfaces and to form with the surfaces a transport zone. The members further include two access apertures extending from an exterior surface of the member inwardly through one of the transport surfaces to the zone and liquid passageways from the zone to the electrodes. Effective, rapid spreading occurs when two drops are deposited within the zone, whereby an ion junction is provided. When the opposed surfaces are grooved in certain preferred configurations, the wave fronts of the spreading liquid can be readily controlled to follow predictable configurations.

Although the described device provides an effective ion bridge, it has been discovered that under certain circumstances, the flow within the transport zone can be too rapid for optimum results. If the rate of flow is too fast, any unintentional delay between the initiation of flow of the first drop and the initiation of flow of the second drop can result in the first drop reaching the aperture of the second drop before the latter is deposited. Contamination of the ISE for the second drop then occurs.

This invention has been developed to provide a solution to the aforementioned aspects.

SUMMARY OF THE INVENTION

This invention is directed to a device providing for reduced rate of capillary liquid flow between two opposed surfaces.

More specifically, in accord with one aspect of the invention there is provided a liquid testing device comprising (a) two opposing surfaces which are spaced apart a distance effective to induce capillary flow of introduced liquid and to create a zone of intended liquid transport, the zone comprising at least two distinct regions at least one of which is a liquid analysis region, and (b) means permitting introduction of liquid into the zone for capillary transport to the regions. The improvement features means located between the two distinct regions for delaying capillary transport of liquid from one of the regions to the other region.

In accord with another aspect of the invention, there is provided a device for controlled liquid flow, the device including two opposing liquid transport surfaces, means spacing the surfaces apart a distance effective to induce capillary flow of introduced liquid and to define a transport zone, and means permitting introduction of liquids into the zone at two spaced-apart locations. The improvement features, in the device, gating means intermediate the locations and extending between the surfaces across a major portion of the zone, for delaying flow of liquid between the two locations.

Such a device is particularly useful in determining the activity of an ionic analyte of an aqueous solution, the two surfaces in such a case being those of a member bridging two solid electrodes as an ion bridge. Thus, in accordance with another aspect of the present invention, there is provided an ion-selective electrode device with a capillary flow bridge member between the electrodes having a reduced rate of capillary liquid flow within the bridge.

In yet another, related aspect of the invention, such a device utilizes the means spacing apart the capillary flow surfaces of the bridge member as the rate control means.

Other features and advantages will become apparent upon reference to the following Description of the Preferred Embodiments when read in light of the attached drawings.

BRIEF DESCRIPTION OF THE DRAWINGS

FIG. 2 is a sectional view taken generally along the vertical plane of line II—II of FIG. 1;

FIG. 4 is a sectional view taken generally along the vertical plane of line IV—IV of FIG. 3;

FIG. 5 is a fragmentary plan view similar to that of FIG. 3, but illustrating an alternate embodiment;

FIG. 6 is a fragmentary sectional view similar to that of FIG. 4 but illustrating yet another embodiment of the invention.

DESCRIPTION OF THE PREFERRED EMBODIMENTS

The embodiments hereinafter described are directed specifically to ion bridges in devices which potentiometrically measure ionic analytes using ISE's. In addition, this invention can be applied to any liquid transport device which relies upon capillary flow between two opposing surfaces to distribute a liquid.

The device of this invention is capable of measuring the activity of various ionic analytes, commonly called electrolytes, found in aqueous solutions. From this measurement the corresponding concentration of the analyte is calculated by known methods using a calibrated relationship.

The embodiments hereinafter described refer to whole blood and blood serum as the preferred test solution. However, any electrolyte of an aqueous solution can be so measured. For example, blood plasma, urine and spinal fluid can be so analyzed.

Figure 1:
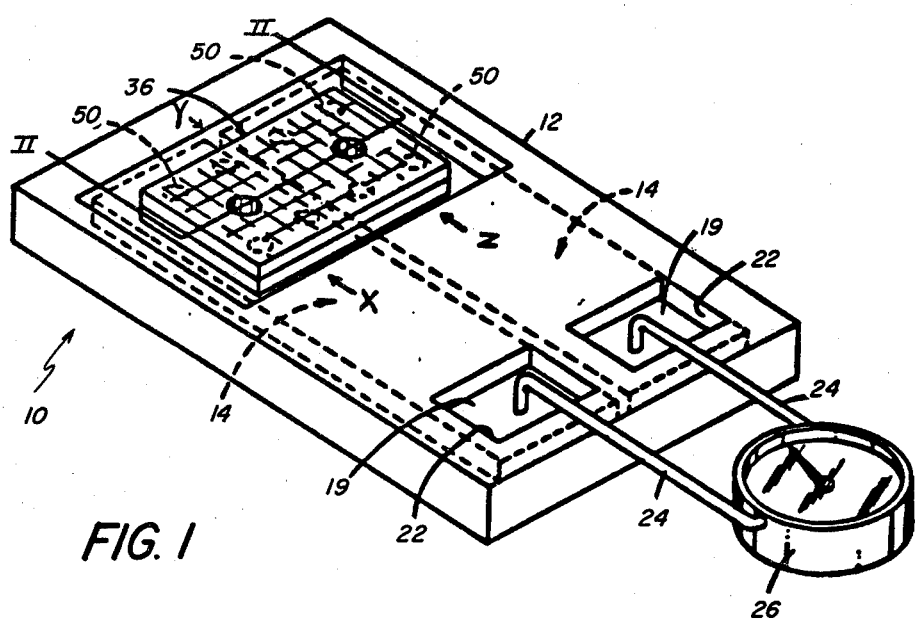
FIG. 1 is an isometric view of an ISE test device.

Preferably the device of this invention includes, FIG. 1, an electrically insulative frame 12 which mounts a spaced-apart pair of preferably solid ion-selective electrodes 14 spanned by a flow control bridge 36. As described in U.S. Pat. No. 4,053,381, issued on Oct. 11, 1977, the details of which are expressly incorporated herein by reference, each ISE is a generally flat multilayered element comprising adjacent layers 16–20, FIG. 2. When a drop of blood serum A or B, FIG. 2, makes contact with layer 16, an ion-selective membrane, the ion $Z(\pm)$ of choice which is an analyte of the blood serum is carried or otherwise penetrates to the underlying layers 17–18. In these layers, an electrical potential is generated proportional to the activity of that particular ion. Layer 17, for example, can be a dried hydrophilic binder containing the salt $Z^{\oplus}X^{\ominus}$. Layer 18 in such instances is the $X^{\ominus}$ salt of an electrically conductive metal $M^{\oplus}$, and metal $M°$ forms layer 19. Because layer 18 is an electrically conductive layer, a potential can be detected by electrometer 26, FIG. 1, via probes 24 which penetrate into contact with layer 19 at windows 22. Any difference in these potentials due to two different ion activities of two liquids A and B, one an unknown and one a reference having a known concentration of $Z(\pm)$, is registered as a difference potential on the electrometer. This reading is then converted into a measure of concentration of the ionic analyte $Z(\pm)$.

Bridge 36 is used to provide means for directing the liquid flow from drops A and B to ISE's 14 and to each other, FIG. 2, as is described in my application Ser. No. 954,689. The bridge insures that an electrical circuit is completed and the potentials generated in the ISE's will register on electrometer 26. The bridge comprises two members 38 and 40 spaced apart in the manner described below. The flow of the drops A and B to ISE's 14 is guided by aligned pairs of cylindrical apertures 27, 27' and 28, 28' in members 38 and 40, respectively, FIG. 2. Apertures 27, 27' extend inwardly from exterior surface 39 of member 38. Apertures 28 and 28' are positioned above and adjacent to the respective ISE 14 to be contacted by the liquid.

Any convenient drop dispenser can supply the drops, either in free-falling form or as drops touched-off from a platform. Preferably, the drops are dispensed simultaneously to insure proper junction formation, as described below.

Members 38 and 40 have opposing internal surfaces spaced apart a distance s, FIG. 2, effective to induce capillary flow of liquid between the surfaces and to define a zone 41 of intended liquid transport or flow. Each surface can be either smooth, or, as shown bear a pattern of exposed grooves 42 and 44, which can be for example sawtooth in shape. If grooves are used, grooves 44 preferably extend from at least the vicinity of aperture 28 to at least the vicinity of aperture 28', and are preferably substantially parallel and straight. Grooves 42 are superimposed over grooves 44 preferably at a positive, that is, non-zero angle alpha. Most preferably alpha is about 90°, and the grooves are also substantially parallel and straight. As shown, grooves 42 and 44 and their ridges 46 and 48 have a width w and thickness t, respectively, the values of which can be varied depending on design choices.

The spacing s is maintained, in the embodiment of FIG. 1 and 2, by studs 50 which extend from the surface of grooves 42 to the surface of grooves 44. These are of small cross-sectional diameter, compared to the overall flow area of zone 41, and can be, as shown, eight in number. As such, they do not significantly impede flow of liquid within zone 41. Preferably studs 50 are formed by ultrasonically welding the two opposed surfaces of members 38 and 40 together, at the locations of the studs, creating, FIG. 2, depressions 51 in exterior surface 39.

Thus, simultaneously applied drops A and B not only penetrate apertures 28 and 28' to contact ISE's 14, they also form two advancing wave fronts in zone 41. If grooves 42 and ridges 46 are linear, so are wave fronts 62. If ridges 46 are parallel throughout bridge 36, the wave fronts when they meet form a straight line junction between apertures 27 and 27', of minimum width.

Departures from the linear, parallel pattern of grooves described above also are effective, it being noted however that the junction between the two liquids will have in those cases a greater width and perhaps a non-linear shape, representing more intermixing of liquids A and B.

It will be appreciated that zone 41 has three discrete regions X, Y and Z, FIG. 1. Each of these regions provides liquid transport, and preferably also liquid manipulation beyond simple transport. As used herein, "manipulation" refers to a step or reaction, other than transport between the opposed surfaces, which can be chemical, physical, or electrical in nature, that takes place in or to the liquid, e.g., a liquid analysis step such as occurs when the liquid flows into contact with an ISE that detects a specific ionic activity of the liquid. Thus regions X and Z are substantially identical, and constitute the region of liquid analysis wherein the two liquids respectively flow through apertures 27 and 27', FIG. 2, to contact the ISE's 14 that are fluidly connected to zone 41 by reason of such apertures. Region Y however is different in that it is the region of the junction of the two wavefronts of drops A and B. It is across this junction that ion exchange, an electro-physical phenomenon, occurs to permit the completion of the electrical circuit formed by ISE's 14 now in contact with drops A and B, and electrometer 26.

Figure 3:
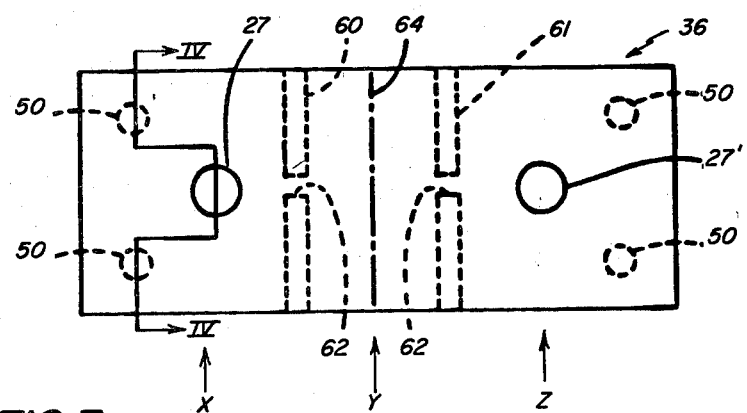
FIG. 3 is a plan view of just the ion bridge member of an ISE test device constructed in accordance with the invention.

In accordance with one aspect of the invention, the device is improved by providing, FIGS. 3 and 4, between at least regions X and Z and/or Y and Z, means for delaying capillary transport of liquid from region X or Z into region Y. "Delaying", as used herein described a generic condition that includes both the temporary cessation of flow as well as continued flow at a reduced rate. Whichever occurs is a function of the configuration of the gating aperture and of the volume of the liquid located "behind" the gate and constituting an equivalent head of pressure. If the gating aperture is the appropriate configuration, even excess liquid beyond that capable of filling the entire transport zone will not cause the meniscus to advance beyond the gating aperture. Preferably, such delaying means are formed as at least one and preferably two walls 60 and 61 extending integrally from and between the opposed surfaces of members 38 and 40. As in the case of studs 50, also used, walls 60 and 61 preferably function to space apart the opposed surfaces by distance s, FIG. 4, and are formed by ultrasonically welding the two surfaces together at appropriate places between apertures 27, 27'. If the apertures 27, 27' are spaced apart lengthwise of zone 41, as shown in FIG. 3, each wall 60 or 61 extends the major portion of the width of zone 41. Preferably it extends the entire width except for a gating aperture 62 formed in each wall by the ultrasonic welding pattern. Such aperture 62 can be located anywhere in walls 60 and 61. The preferred location is in that portion of the wall directly interposed in the path of liquid flow that would otherwise occur from aperture 27 to aperture 27', as shown.

The two gating apertures 62 in walls 60 and 61 serve to markedly reduce the rate of flow in zone 41 of the two drops deposited in apertures 27 and 27' at regions X and Z, FIG. 3. The formation of the junction between the two drops, designated by a broken line 64 in region Y, is thus delayed. Thus there is little likelihood that one or the other of the two drops will inadvertently race over to the other aperture prior to the second drop spreading outwardly from its access aperture. Or, FIG. 2, drop A is restricted from flowing so rapidly that it proceeds all the way from aperture 27 to aperture 28' prior to drop B spreading from aperture 28. There is however no change in the flow of the liquids through apertures 27, 27' or passageways 28 and 28', or to their respective ISE's 14, shown in phantom, FIG. 4.

Only one of the opposed surfaces is shown as containing grooves 42, the other being smooth as at 70. Alternatively both can be grooved, or both can be smooth.

Any material can be used to form the bridge members, and thus the gating walls, but preferably they are selected from plastics that can be ultrasonically welded. Examples include acetates such as cellulose triacetate and the like, polystyrene, etc.

Any conventional ultrasonic horn can be used to form the gating walls. Such horns are driven, as is well known, by a transducer which translates electrical signals into high frequency vibrations. As will be clearly apparent, the edge of the horn in contact with the bridge 36 should have the shape desired for the gating walls. Typically, ultrasonic energy of 60 to 80 watts can be applied by such a device for about 40 to 50 milliseconds when using the above-noted materials.

It will be appreciated that walls 60, because of their considerable extension across the width of zone 41, serve to more adequately maintain the preferably planar alignment of members 38 and 40 than can be achieved by studs 50 alone.

Preferably the zone 41 of intended liquid transport is a void zone. This term is used herein to mean, a zone void of other solids or liquids, or which contains such solids or liquids in an amount less than 50% of the total volume of the zone. As an example of the latter, coaxial fibers can be included in regions X, Y or Z separately, extending in the direction of liquid flow, provided the amount thereof is less than 50% of the total volume of the transport zone.

In an alternate embodiment, region Y of FIG. 3 can have pre-applied to it, between the opposing gating walls 60 and 61, and on either or both of the opposite surfaces 42 or 70, FIG. 4, a coating of an equitransferent salt of the type described in U.S. Pat. No. 4,053,381 issued on October, 11, 1977. The salt redissolves in the presence of the two liquids added to apertures 27 and 27', and forms a salt solution that acts to suppress junction potentials that otherwise form when the two liquids meet in region Y.

Although regions X and Z are disclosed as potentiometric liquid analysis regions, it will be apparent that other kinds of analysis regions can be used in other environments, for example, radiometric analysis regions. Also, a region can be used to permit a chemical reaction or one of a plurality of sequential chemical reactions, such reactions requiring, for example, a time delay as provided by the delaying means of the invention that is disposed between the chemical reaction region and the region of liquid transport that is upstream thereof. Still further, two adjacent regions separated by the delaying means of the invention can both be liquid analysis regions, one of which permits analysis prior to the other, e.g., as in the determination of rate reactions.

In the embodiment of FIG. 5, the gating wall is formed with the gating aperture at one side. Parts similar to those previously described bear the same reference numeral to which the distinguishing suffix "a" is appended. Thus bridge 36a has liquid access aperture 27a and studs 50a separating the two members of the bridge, as before. However, wall 60a is formed with aperture 62a located at the side of the bridge. In such an arrangement, liquid flow follows arrow 72. This location of the gating aperture still permits zone 41a to fill with the two liquids with a junction between them, not shown.

The gating aperture can be any shape and size, so long as its configuration will allow liquid flow through or around the gating wall at a restricted rate that is less than the rate that would occur in the absence of the gate. Thus, as in FIG. 6, gating aperture 62b in wall 60b of bridge 36b can be circular. A preferred width, or in the case of aperture 62b, the diameter, of the aperture is about 0.2 to about 1 mm.

Figure 7:
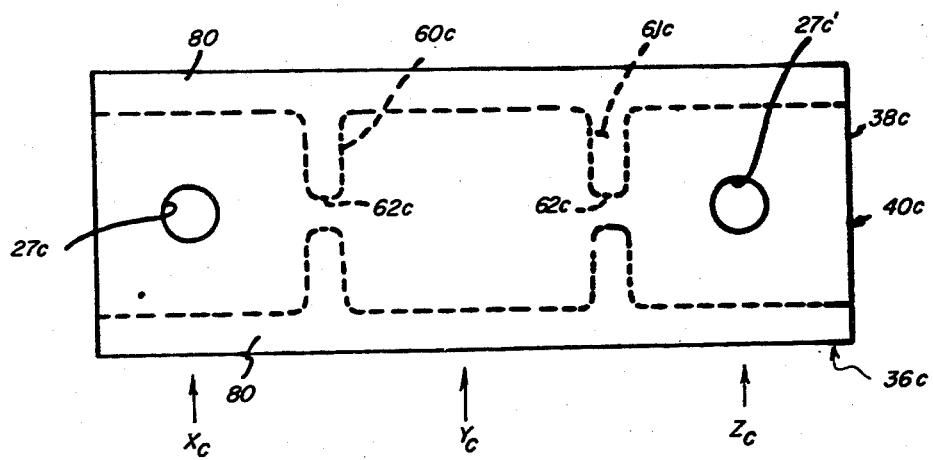
FIG. 7 is a plan view similar to that of FIG. 3 but illustrating still another embodiment.

In the embodiment of FIG. 7, the spacer or gating walls have been extended to completely enclose the side portions of the bridge. Parts similar to those described bear the same reference numeral to which the distinguishing suffix "c" has been added. Thus, bridge 36c is provided with gating walls 60c and 61c disposed between apertures 27c and 27c' and between regions Xc, Yc and Zc, Yc, respectively. These walls join together and space apart members 38c and 40c along the entire side portions 80 of the bridge. As before, apertures 62c are left in the center portion of walls 60c and 61c to allow a restricted rate of flow between the apertures.

The invention has been described in detail with particular reference to certain preferred embodiments thereof, but it will be understood that variations and modifications can be effected within the spirit and scope of the invention.

What is claimed is:

1. In a liquid testing device comprising
   (a) two opposing surfaces which are spaced apart a distance effective to induce capillary flow of introduced liquid and to create a void zone of intended liquid transport, said zone comprising at least two distinct regions, at least one of which is a liquid analysis region, and
   (b) means permitting introduction of liquid into said zone for capillary transport to said regions,
the improvement comprising gating means located between said two distinct regions for delaying capillary transport of liquid through said zone from one of said regions to other of said regions, said gating means including a gating wall extending across the intended path of liquid flowing from one of said regions to the other so as to delay liquid flow along said path, said wall including a gating aperture therein that is free of fibers.

2. In a liquid testing device comprising
   (a) two opposing surfaces which are spaced apart a distance effective to induce capillary flow of introduced liquid and to create a void zone of intended liquid transport, said zone comprising at least two distinct regions at least one of which is a liquid analysis region, (b) an ion-selective electrode fluidly connected to said one liquid analysis region, and (c) means permitting introduction of liquid into said zone for capillary transport to said regions, the improvement comprising gating means located between said two distinct regions for delaying capillary transport of liquid through said zone from one of said regions to other of said regions.

3. A device as defined in claim 1 or 2, wherein said delaying means retards but does not stop transport of liquid from one of said regions to the other of said regions.

4. A device as defined in claim 1 or 2, wherein said gating means includes two walls, each extending across said transport zone and having a gating aperture therein.

5. A device as defined in claim 4, wherein said permitting means includes two access apertures spaced along the length of said zone, and wherein each of said walls is located in the path of liquid flow between said access apertures.

6. A device as defined in claim 1 or 2, wherein at least one of said opposed surfaces includes, across at least a portion thereof, a plurality of exposed grooves.

7. In a liquid transport device for controlled liquid flow, the device including two opposing liquid transport surfaces, means spacing said surfaces apart a distance effective to induce capillary flow of introduced liquid and to define a transport zone, and means permitting introduction of liquids into said zone at two spaced-apart locations; the improvement comprising:

a pair of gating means disposed to intercept liquid flow in said zone between said locations, each of said gating means including gating aperture means sized to allow liquid flow to continue at a restricted rate.

8. A device as defined in claim 7, wherein each of said gating means comprises a wall integrally extending from a separating said surfaces, positioned adjacent to a respective one of said locations, said wall having a gating aperture therein.

9. A device as defined in claim 7, wherein at least one of said transport surfaces includes, across at least a portion thereof, a plurality of exposed grooves.

10. In a device for determining activity of an ionic analyte of an aqueous solution, said device including a pair of solid electrodes each constructed to develop therein an electric potential that is proportional in magnitude to the amount of analyte activity present in a contacting drop of said solution;

and flow control means for directing liquid flow from a drop of an aqueous solution to at least one of said electrodes, said control means including (a) a member bridging and contacting said two electrodes and comprising two opposed liquid transport surfaces and means spacing apart said surfaces a distance effective to induce capillary flow of introduced liquid between said surfaces and to form with said surfaces a transport zone having a predetermined width and length, and (b) means permitting introduction of liquids into said zone at two spaced-apart locations;

the improvement wherein said spacing means includes gating means intermediate said locations and extending between said surfaces across a major portion of said zone, for delaying flow of liquid within said zone between said locations, said gating means including gating aperture means sized to provide restricted liquid flow between said two locations.

11. A device as defined in claim 10, wherein said gating means includes two walls each extending across said transport zone and having a gating aperture therein.

12. A device as defined in claim 11, wherein said permitting means include two access apertures spaced along the length of said zone and extending from an exterior surface of said member inwardly through one of said transport surfaces to said transport zone, and wherein each of said walls is located between said apertures.

13. In a device for determining activity of an ionic analyte of an aqueous solution, said device including a pair of solid electrodes each constructed to develop therein an electrical potential that is proportional in magnitude to the amount of analyte activity present in a contacting drop of said solution;

and flow control means for directing liquid flow from a drop of an aqueous solution to at least one of said electrodes, said control means including (a) a member bridging said two electrodes and comprising two opposed liquid transport surfaces spaced apart a distance effective to induce capillary flow of introduced liquid between said surfaces and to form with said surfaces a transport zone, and (b) means permitting introduction of liquids into said zone at two spaced-apart locations; the improvement comprising:

gating means disposed to intercept liquid flow in said zone between said locations, for delaying liquid flow through said zone, said gating means including gating aperture means sized to allow liquid flow to continue at a restricted rate between said two locations.

14. A device as defined in claim 13, wherein said gating aperture means is directly interposed in the path of liquid flow between said locations.

15. A device as defined in claim 13, wherein at least one of said transport surfaces includes, across at least a portion thereof, a plurality of exposed grooves.

16. In a device for determining activity of an ionic analyte of an aqueous solution, said device including a pair of solid electrodes each constructed to develop therein an electrical potential that is proportional in magnitude to the amount of analyte activity present in a contacting drop of said solution;

and flow control means for directing liquid flow from a drop of an aqueous solution to at least one of said electrodes, said control means including (a) a member bridging said two electrodes and comprising two opposed liquid transport surfaces spaced apart a distance effective to induce capillary flow of introduced liquid between said surfaces and to form with said surfaces a transport zone, and (b) means permitting introduction of liquids into said zone at two spaced-apart locations; the improvement comprising:

a pair of gating means disposed across the path of liquid flow in said zone between said two locations for delaying liquid flow through said zone, each of said gating means including gating aperture means sized to allow liquid flow to continue at a restricted rate between said locations.

17. A device as defined in claim 16, wherein each of said gating means comprises a wall integrally extending from and separating said surfaces and having a gating aperture therein.

18. A device as defined in claim 16, wherein said gating aperture are directly interposed in the path of liquid flow between said locations.

19. A device as defined in claim 16, wherein at least one of said transport surfaces includes, across at least a portion thereof, a plurality of exposed grooves.

* * * * *